United States Patent
Wikeley et al.

(10) Patent No.: US 9,968,088 B2
(45) Date of Patent: May 15, 2018

(54) PLANT GROWTH REGULATING COMPOSITION AND METHODS FOR MAKING AND USING SAME

(71) Applicants: Phil Wikeley, Worcestershire (GB); Kevin Forney, Bakersfield, CA (US); Greg Johnson, Alamo, CA (US)

(72) Inventors: Phil Wikeley, Worcestershire (GB); Kevin Forney, Bakersfield, CA (US); Greg Johnson, Alamo, CA (US)

(73) Assignee: Fine Agrochemicals Ltd., Worcestor (GB)

(*) Notice: Subject to any disclaimer, the term of this patent is extended or adjusted under 35 U.S.C. 154(b) by 0 days. days.

(21) Appl. No.: 14/485,166

(22) Filed: Sep. 12, 2014

(65) Prior Publication Data

US 2015/0080216 A1 Mar. 19, 2015

Related U.S. Application Data

(60) Provisional application No. 61/877,474, filed on Sep. 13, 2013.

(51) Int. Cl.
*A01N 43/90* (2006.01)
*A01N 43/08* (2006.01)
*A01N 43/38* (2006.01)
*C05G 3/00* (2006.01)
*A01N 45/00* (2006.01)
*A01N 25/14* (2006.01)

(52) U.S. Cl.
CPC ............ *A01N 43/90* (2013.01); *A01N 25/14* (2013.01); *A01N 43/08* (2013.01); *A01N 43/38* (2013.01); *A01N 45/00* (2013.01); *C05G 3/00* (2013.01)

(58) Field of Classification Search
CPC ........ A01N 43/38; A01N 43/90; A01N 37/02; A01N 45/00; A01N 25/14; A01N 43/08; C05G 3/00
USPC .......................................................... 504/136
See application file for complete search history.

(56) References Cited

U.S. PATENT DOCUMENTS

| | | | | |
|---|---|---|---|---|
| 3,778,247 A * | 12/1973 | Pyne | ................ | C07D 295/215 504/287 |
| 3,961,932 A * | 6/1976 | Miller | ................ | C05B 1/02 71/1 |
| 4,507,144 A | 3/1985 | Aloni | | |
| 4,936,901 A | 6/1990 | Surgant, Sr. et al. | | |
| 5,188,655 A * | 2/1993 | Jones | ................ | A01N 43/90 504/136 |
| 5,622,658 A | 4/1997 | Lloyd et al. | | |
| 6,984,609 B2 | 1/2006 | Devisetty et al. | | |
| 8,819,989 B2 * | 9/2014 | Paternoster | ......... | A01G 9/1086 47/58.1 R |
| 2003/0008949 A1 * | 1/2003 | Devisetty | ............. | A01N 25/12 524/56 |
| 2007/0180877 A1 | 8/2007 | Anderson et al. | | |
| 2009/0156404 A1 * | 6/2009 | Kupatt, Jr. | ............ | A01N 37/02 504/324 |
| 2010/0216641 A1 | 8/2010 | Wang et al. | | |
| 2011/0230353 A1 * | 9/2011 | Anderson | ............ | A01N 25/12 504/320 |

FOREIGN PATENT DOCUMENTS

| | | |
|---|---|---|
| CN | 101703073 A | 5/2010 |
| EP | 0 252 897 A2 | 1/1988 |
| GB | 2 401 863 A | 11/2004 |
| WO | 02/082902 A2 | 10/2002 |
| WO | 2005/060755 A1 | 7/2005 |
| WO | 2010/099428 A1 | 9/2010 |

OTHER PUBLICATIONS

International Search Report and Written Opinion of the International Searching Authority dated Dec. 17, 2014 for PCT Patent Application No. PCT/US2014/055428, 10 pages.
Search and Examination Report for GB Patent Application No. 1416279.6 dated Feb. 27, 2015, 6 pages.
Blunden, G. et al. (1979). "The Effects of Aqueous Seaweed Extract on Sugar Beet," *Botanica Marina* XXII: 539-541.
Williams, D.C. et al. (1974). "Plant Growth Regulatory Substances in Commercial Seaweed Extracts," *Proceedings of the Eighth International Seaweed Symposium*, Bangor, North Wales, Aug. 18-23, 1974, pp. 760-763.
Blunden, G. (1977). "Cytokinin Activity of Seaweed Extracts," *Marine Natural Products Chemistry* 1:337-344.
Office Action issued in Chinese Application No. CN201480062245. 5, dated Mar. 13, 2017, 12 pages.
Office Action issued in Australian Application No. AU2014318558, dated Mar. 21, 2017, 3 pages.

* cited by examiner

*Primary Examiner* — Johann R Richter
*Assistant Examiner* — Courtney Brown
(74) *Attorney, Agent, or Firm* — Kilpatrick Townsend & Stockton LLP

(57) ABSTRACT

Water soluble plant growth regulating compositions in granule form and methods for making and using same. The granules comprise an active medium, a carrier medium and optionally a surfactant, wherein the active medium comprises: a gibberellin, a cytokinin, and an auxin. The inventive compositions are shelf stable and may be completely dissolved in water prior to application on a plant or seed.

24 Claims, No Drawings

PLANT GROWTH REGULATING COMPOSITION AND METHODS FOR MAKING AND USING SAME

CROSS-REFERENCE TO RELATED APPLICATION

This application claims priority to U.S. Provisional Application No. 61/877,474, filed on Sep. 13, 2013, the entirety of which is incorporated herein by reference.

FIELD OF THE INVENTION

The present invention relates generally to water-soluble plant growth regulating compositions in granule form, and more particularly to growth regulating compositions comprising an active medium, a carrier medium and optionally a surfactant, wherein the active medium comprises a gibberellin, a cytokinin, and an auxin.

BACKGROUND OF THE INVENTION

Plant growth regulators such as auxins, cytokinins, and gibberellins are useful for influencing a range of plant developmental processes including stem elongation, germination, dormancy, flowering, sex expression, enzyme induction, fruit size and quality, as well as leaf and fruit senescence.

For example, there are known growth stimulators based on naturally occurring and synthetic auxins, such as indoleacetic acid and naphthaleneacetic acid, which induce stem elongation and promote root formation. Other synthetic auxins include 4-chloro-2-methylphenoxyacetic acid (MCPA); 2,4-chlorophenoxyacetic acid (2,4D); 2,4,5-trichlorophenoxyacetic acid (2,4,5-T); 2-(4-chloro-2-methyl-phenoxy) propionic acid (CMPP); 4-(2,4-dichlorophenoxy) butyric acid (2,4-DB); 2,4,5-trichlorobenzoic acid (TBA); and 3,5-dichloro-2-methoxybenzoic acid (dicamba), for example. All the above acids are active in the form of their salts and esters, such as their sodium, potassium, ammonium, dimethylamine and ethanolamine salts, and their lower alkyl esters. Many of these synthetic auxins are being used commercially as effective herbicides and some of them are known to adversely affect morphogenesis of treated plants. Some auxins, however, such as 3-indolebutyric acid (3-IBA), have been shown to exhibit high instability in aqueous systems.

Preparations based on cytokinins, such as 6-furfurylamino purine and 6-benzlyamino purine, are also known to be growth stimulators. However, cytokinins-based preparations which have a decisive influence in the stimulation of cell division seldom produce a desirable effect in the absence of auxins. While the mechanism by which cytokinins affect the growth cycle of plants is far from being understood, it is apparent that they affect leaf growth and prevent aging in certain plants. While the action of cytokinins on the growth of cultivated plants has been extensively studied, these plant hormones did not find wide application in plant raising since they must be applied at specific concentrations in parts per million. These critical rates of application render cytokinins-based preparations highly impractical in an agricultural environment.

Of all the known stimulators, the most widely used is a series of natural plant hormones generically named "gibberellins". The gibberellins are used for the acceleration or regulation of various stages of plant development, particularly growth, efflorescence, germination and parthenocarpy of higher plants. A series of related compounds identified as gibberellin $A_1$ through $A_{44}$ has been obtained by microbiological synthesis and the various compounds isolated from culture broth of *Gibberella fujikuroi* and from various plants including certain beans. The main component of the gibberellins used in practice is gibberellin $A_3$, otherwise known as gibberellic acid.

While gibberellins are highly effective as plant growth promoting or regulating substances, their use is greatly limited by their expense and insufficient effectiveness at low concentrations. As a result, considerable research has concentrated on efforts to find synergistic agents which can be used to enhance the activity of gibberellins. One such synergistic agent for use with the gibberellins that have been discovered and put to practical use is described in U.S. Pat. No. 4,507,144 to Aloni. This patent discloses a composition consisting of the auxin naphthaleneacetic acid (NAA) and gibberellic acid ($GA_3$) used for application to growing plants in order to increase the fiber content of the plants. However, the patented composition does not find wide application in plants other than those disclosed as being used as a source of commercial fibers and show little efficiency in stimulating growth, flowering and fructification of horticultural crops. Moreover, since the disclosed composition is applied to the plant as an aqueous spray, appreciably quantities of the composition flows down onto the soil and is not absorbed and assimilated in a systemic manner by the plant. Another disadvantage of the particular aqueous composition described by Aloni, which is especially specific when a spraying technique is employed, is the reduction of crop quality caused by the impossibility of attaining equally uniform application of the aqueous spray to various parts of the treated plant. A further disadvantage resides in the relatively high water requirements for the preparation of the reference compositions, the consumption of water being up to 800 liters per hectare.

Gibberellin solution formulations are disadvantageous in several respects. The solutions, such as those of $GA_{4+7}$ in propylene glycol, are less concentrated due to low solubility of actives, and have limited stability. Of the currently used solvents, isopropyl alcohol and methyl alcohol offer severe disadvantages such as flammability and toxicity, which lead to restrictions in manufacturing, packaging, labeling, transportation, and warehousing of such solutions. THFA, used in some of the formulations, is considered corrosive to the eye and skin. Moreover, low solubility of gibberellins in propylene glycol does not permit preparation of high potency solution formulations. These low strength solution formulations also require larger packaging, more storage space, and higher associated transportation, warehousing, and container disposal costs. Due to very low solubility and undesirable hydrolysis, it has not been possible to formulate gibberellins in aqueous systems.

Some plant growth regulators may be prepared as water-dispersible granules. To prepare the water-dispersible granules for spray application, they are dispersed in water and form a suspension upon agitation. Many different water-dispersible granular formulations are known for agricultural chemicals. For example, EP 0 252 897 and U.S. Pat. No. 4,936,901 disclose encapsulated plant growth regulators in water dispersible granular formulations; and U.S. Pat. No. 5,622,658 discloses an extrudable composition for preparing water-dispersible granules. U.S. Pat. No. 6,984,609 discloses a water-soluble granular composition including at least 40% of at least one gibberellin as plant growth regulator, at least one binder, at least one disaccharide and at least one surfactant.

Water-dispersible granules usually have no greater than eight percent moisture content, and form suspensions when added to aqueous solutions. The resulting suspension must be agitated for a period of time in order to fully disperse it. Agitation or by-pass recirculation of the tank-mix must also be maintained during application. The quality of water-dispersible granules is highly process- and active-ingredient-dependent and can result in low yield recoveries, poor attrition resistance leading to dust potential, high manufacturing cost and poor dispersion. Generally, sprays of dissolved water-dispersible granular formulations leave undesirable insoluble residues on the treated foliage and fruit.

For plant growth regulators such as gibberellins to be efficacious, the active ingredient must solubilize in the tank-mixes prior to application. Otherwise, product efficacy will be severely affected. When water-dispersible granules are used, the grower often may not be able to realize if he had achieved the total solubility of the active ingredient in the spray solutions. In addition, water-dispersible granules can become hardened over time and thus result in poor dispersibility and solubility of the active ingredient. Dust and caking may be problems with certain water-dispersible granules and powder formulations.

Attempts have been made to combine various plant growth regulators into a single formulation. U.S. Pat. No. 5,188,655, for example, discloses a mixture of gibberellins, the heteroauxin indole-3-acetic acid and the cytokinin 6-(4-hydroxy-3-methyl-2-trans-betenylamino)purine in definite proportions. In addition to the aforementioned problems with plant growth regulating granules, compounding gibberellins with other certain other plant growth regulators, however, has been shown in particular to increase granule instability and reduce solubility. Therefore, the need exists for plant growth regulator formulations that provide high potency and rapid solubility and avoid the problems associated with conventional formulations.

SUMMARY OF THE INVENTION

In one embodiment, the invention is a water-soluble plant growth regulating composition in granule form, comprising an active medium, a carrier medium and optionally a surfactant, wherein the active medium comprises a gibberellin, a cytokinin, and an auxin. Preferably, the composition has a solubility greater than 1 g/100 g water, e.g., greater than 5 g/100 g water or greater than 10 g/100 g water, at 25° C.

The gibberellin optionally is selected from the group consisting of $GA_3$, $GA_4$, $GA_5$, $GA_7$ and combinations thereof. The cytokinin optionally is selected from the group consisting of kinetin, 6-BAP, 1-(2-chloropyridin-4-yl)-3-phenylurea (CPPU), and TDZ. The auxin optionally is selected from the group consisting of 3-indolebutyric acid, 3-indoleacetic acid, 1-naphthylacetic acid, 3-indolebutyric acid, and salts and esters thereof. The optional surfactant is preferably selected from the group consisting of: alkylnaphthalene sulphonates, Oxoalcohol PO-EO adducts, and salts and mixtures thereof, and optionally in an amount from 1 to 20 weight percent.

The composition may comprise one or more micronutrients, e.g., chelating agents, optionally selected from the group consisting of ethylene diamine tetra-acetic acid (EDTA) and citrate salts. The one or more optional micronutrients may comprise one or more nitrogen sources.

The composition optionally comprises the gibberellin in an amount from 0.001 to 10 wt. %, the cytokinin in an amount from 0.001 to 10 wt. % and the auxin in an amount from 0.001 to 10 wt. %, based on the total weight of the granules.

In one aspect, the gibberellin comprises gibberellin $GA_4$, the cytokinin comprises kinetin, and the auxin comprises indole-3-butyric acid. In some aspects, the gibberellin comprises a mixture of gibberellin $GA_4$ and gibberellin $GA_7$.

The active medium may have an average particle size from 1 to 5 µm as determined by laser diffraction particle size analysis.

The carrier medium preferably comprises lactose monohydrate.

The granules optionally comprise the carrier medium in an amount from 70 to 99 wt. %, based on the total weight of the granules. The carrier medium preferably is water soluble.

In another embodiment, the invention is to a process for preparing a liquid plant growth regulating composition, comprising dissolving any of the aforementioned compositions in water to form the liquid plant growth regulating composition. In this embodiment, the water may be provided in an amount sufficient to provide an auxin concentration from 0.3 to 10.5 wppm, a cytokinin concentration from 0.6 to 20.9 wppm and a gibberellin concentration from 0.2 to 7.0 wppm (wppm being ppm on a weight basis).

In another embodiment, the invention is to a process for regulating plant growth comprising: (a) dissolving the composition as described above in general or preferred and/or optional embodiments, in water to form a liquid plant growth regulating composition; and (b) applying the liquid plant growth regulating composition to a plant or seed. Step (b) optionally comprises applying the liquid plant growth regulating composition to a seed, the process further comprising planting the seed. Alternatively, step (b) comprises applying the liquid plant growth regulating composition to a seed furrow during a planting operation. Alternatively, step (b) comprises applying the liquid plant growth regulating composition to a plant.

In another embodiment, the invention is to a process for making a water-soluble plant growth regulating composition in granule form, the process comprising the steps of: (a) powder blending a gibberellin, a cytokinin, an auxin, a carrier medium and optionally a surfactant to form a powder mixture; (b) adding water to the powder mixture in an amount sufficient to form an extrudable paste; (c) extruding the paste to form an extrudate; (d) cutting the extrude to form wet granules; and (e) drying the wet granules to a water content less than 5 wt. % and forming the plant growth regulating composition in granule form. The process optionally further comprises hammer milling the gibberellin, the cytokinin and the auxin prior to the blending step.

DETAILED DESCRIPTION OF THE INVENTION

The present invention relates to a water-soluble plant growth regulating composition in granule form, comprising an active medium, a carrier medium and optionally a surfactant, wherein the active medium comprises a gibberellin, a cytokinin, and an auxin. It has now been discovered that compositions containing these plant growth regulators may be advantageously prepared in stable water-soluble granule form even at high gibberellin loading levels. The invention also relates to processes for making and using such plant growth regulating compositions. The composition desirably has an overall solubility greater than 1 g/100 g water, e.g., greater than 5 g/100 g water or greater than 10 g/100 g water, at 25° C.

As used herein, the term "granule" refers to a solid composition comprising particles, preferably extruded particles, having an average particle size (diameter for substantially spherical particles or cylindrical extrudates) from 0.5 to 3.0 mm, e.g., from 0.5 to 2.0 mm or from 0.9 to 1.5 mm, as determined by sieve selection. The granules are preferably formed by milling all solid components to micron size, e.g., 1 to 10 µm, e.g., 1 to 5 µm, followed by addition of water and optionally a surfactant and/or other additives, e.g., binder. The resultant mixture is preferably extruded through a screen (e.g., type 0.5-3.0, from 0.5 to 20 or from 0.9 to 1.5 mm screen) and dried to form the granule compositions of the invention. In case of cylindrical extrudates, the length preferably is about the same size ranges as described for the diameter of the particles. The active medium is thereby bound to carrier particles, optionally surfactant and any other desired adjuvants. The active medium preferably is homogenously distributed throughout the granule.

Gibberellins

The term "gibberellins" encompasses diterpenoids having a tetracyclic ring system. In terms of their nomenclature, gibberellins were numbered in order of their discovery, so the numbering does not signify the position any particular substituent. The compounds have nineteen or twenty carbon atoms, and four or five ring systems. Exemplary gibberellins include $GA_3$, commonly referred to as gibberellic acid; and $GA_4$ and $GA_7$, which are immediate precursors of $GA_3$. There are approximately 90 gibberellins, and, as used herein, all are encompassed by the general term "gibberellin", "gibberellins" or "gibberellic acid." In the formulations, either a single gibberellin or a combination of two or more gibberellins may be employed in the active medium. The gibberellin(s) may preferably be selected from the group consisting of gibberellin $A_2$ ($GA_2$), gibberellin $A_3$ ($GA_3$), gibberellin $A_4$ ($GA_4$), gibberellin $A_5$ ($GA_5$), gibberellin $A_7$ ($GA_7$), gibberellin $A_{14}$ ($GA_{14}$), and mixtures thereof; more preferably selected from the group consisting of $GA_3$, $GA_4$, $GA_5$, $GA_7$ and combinations thereof.

Preferred gibberellin combinations include $GA_4$ and $GA_7$ (preferably in a weight ratio of from 1.5:1 to 99:1, e.g., from 1.5:1 to 15:1 or from 2:1 to 10:1), When stored for extended periods in water, $GA_7$ tends to hydrolyze. Hence, the solid granulation composition of the present invention advantageously provides for increased shelf life over conventional liquid formulations when the gibberellin employed includes $GA_7$.

Cytokinins

The active medium also comprises one or more cytokinins, which is a class of plant growth substances (phytohormones) that promote cell division, or cytokinesis, in plant roots and shoots. There are two types of cytokinins: adenine-type cytokinins represented by kinetin, zeatin, and 6-benzylaminopurine (also referred to as BAP, 6-BAP, or 6-benzyladenine), and phenylurea-type cytokinins like diphenylurea and thidiazuron (TDZ). In preferred embodiments the cytokinin is selected from the group consisting of kinetin (synthetic or derived from seaweed), 6-BAP, 1-(2-chloropyridin-4-yl)-3-phenylurea (CPPU), and TDZ.

Kinetin was the first of the active cytokinins (having growth promoting properties) identified and is a 6-furfurylaminopurine having the formula:

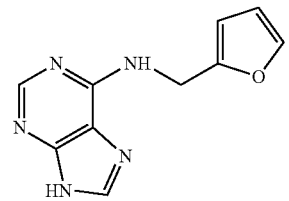 [SMILES: c1coc(CNc2ncnc3[nH]cnc23)c1]

Other naturally occurring cytokinins include dimethlallyl amino purine:

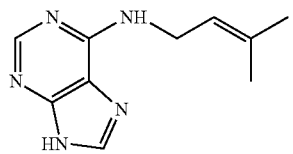

methylamino purine:

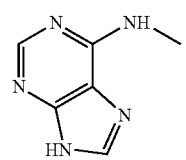

and zeatin(methylhydroxymethylallylaminopurine):

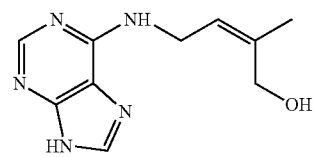 [SMILES: C/C(=C/CNc1ncnc2[nH]cnc12)CO]

Zeatin has been isolated and chemically identified from young kernals of maize, coconut milk, plums, fungus, bacterium, lupin plants and other plants having soluble ribonucleic acid.

One may also find attached to the amino group phenyl, benzyl, n-ethyl, n-propyl, n-butyl and similar groups.

Diphenylurea, a synthetic compound, shown below, also exhibits cytokinin activity.

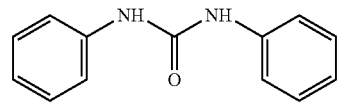 [SMILES: O=C(Nc1ccccc1)Nc1ccccc1]

Another synthetic cytokinin is 6-benzylaminopurine (benzyl adenine or BAP), which has the structure:

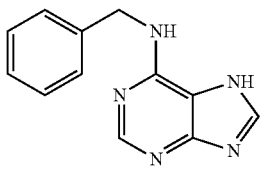 [SMILES: c1ccc(CNc2ncnc3nc[nH]c23)cc1]

Various cytokinins are found in different sources. Dimethylallylaminopurine occurs in soluble ribonucleic acid of many different organisms and is produced by bacterium *corynebacterium fasians*.

The bacterium and mutations from dimethylallylaminopurine invade green plants such as algae, chlorella, kelp and by secreting the compound produces cytokinin effects.

The dihydro-derivative of zeatin has been isolated from lupin plants and cytokinins have been isolated from the sporophyte of mosses.

The richest natural sources for kinins that have been isolated are seaweed, fruits, and endosperm tissues.

Diphenylura in the presence of casein hydrolysate is distinctively active in cytokinin effects.

Cytokinins are strong promoters of bud growth and leaf growth stimulation. Some other effects of cytokinins in plants result in ending dormancy, promoting polarity of growth, promoting flowering, increasing effectiveness of light in germination, and promoting stem elongation.

Auxins

There are many synthetic chemicals that behave like the naturally occurring auxins produced by plant enzyme systems, and the term "auxin" and "auxins" as used herein refers to such compounds in natural and synthetic form. In addition to indoleacetic acids, indol-3-butyric acid (3-BA); naphthaleneacetamide; 2 methyl-1-naphthaleneacetic acid and 2-methyl-1-naphthylacetamide have hormonal activity and may be substituted for the naturally occurring auxins. The synthetic auxins cannot function without zinc, manganese, and other minerals in the same requirement pattern as found with naturally occurring auxins. For best results, the minerals should be in the form of proteinates. The proteinate preferably has a peptide (—CONH—) bond. In preferred embodiments, the auxin employed is selected from the group consisting of 3-indolebutyric acid, 3-indoleacetic acid, 1-naphthylacetic acid (NAA), 3-indolebutyric acid, and salts and esters thereof, for example sodium 1-naphthylacetic acid.

One of the important aspects of plant growth and nutrition is nitrogen fixation. Nitrogen can enter biological systems only when it has been combined with other elements such as hydrogen and oxygen. Industrially nitrogen is converted into such compounds as ammonia, nitrate salts, urea or ammonium sulfate. Nature provides a way for nitrogen fixation using the molecular nitrogen gas ($N_2$) from the air and enzymatically combining it with hydrogen from carbohydrates or natural gas to form ammonia utilizing a nitrogenase. Certain bacteria also act to form ammonia. No substances between nitrogen and ammonia have been isolated, so all the intermediate states must be bound to the nitrogenase.

In the soil fixed nitrogen is employed in the synthesis of biological molecules. A critical structural element is the peptide bond (—CONH—) which links one amino acid to the next; the bond connects a nitrogen atom in one amino acid to a carbon atom in another. Several amino acids may be linked together to form a peptide or polypeptide which will ultimately form a protein.

A metal proteinate not only provides the plant with an essential trace metal but also has a nitrogen fixation sparing effect thus avoiding several steps in nitrogen fixation and allows the plant to absorb ligands containing the peptide bonds directly. This may be accomplished by means of soil application or foliar spray.

Phytohormones may be prepared synthetically or naturally. Cytokinins are primarily available as seaweed extracts. These extracts are diluted with water and used as foliar sprays or applied to the soil.

Kinetin may be prepared synthetically and has essentially the same activity as cytokinin. Gibberellin(s) have also been obtained from seaweed extracts but store less well than cytokinins or kinetin. Auxins have also been prepared from seaweed extracts.

Several beneficial aspects have been attributed to phytohormones including increased crop yields, improved seed germination, increased resistance of plants to frost, fungal and insect attack, increased uptake of inorganic constituents from the soil, reduction in storage losses of fruit and stabilization of chlorophyll. See Blunden, Marine Natural Products Chemistry, Plenum Publishing Corporation, N.Y., N.Y., 1001, pp 337-344.

Phytohormones are known carriers of certain inorganic substances into a plant but the amount of minerals is only a minute fraction of the total mineral requirement for the plant.

According to Brain et al., The Effects of Aqueous Seaweed Extract on Sugar Beet, Proceedings of the Eighth International Seaweed Symposium, University of North Wales, 1974, seaweed extracts are characterized by their high cytokinetic activity. The most important effects of cytokinins are on cell division, cell enlargement, the delaying of senescense and the related transport of nutrients.

One important factor is that cytokinins are very restricted in their movement within the plant, if indeed they move at all from the original site of application. Treated foliar areas act as metabolic sinks and amino acids, phosphates and other substances accumulate in the plant tissues directly under or close to the site of application. For optimal results the cytokinin or other phytohormones should spread throughout the plant. More is involved with phytohormones than the mere mobilization of nutrients, since the delay of senescence of excised plant parts has been demonstrated many times.

The observation that cytokinin treatment augmented the ratio of RNA to DNA, suggested that a critical effect of cytokinins in senescence might be the maintenance of the protein synthesizing machinery, perhaps by regulating RNA synthesis.

Insofar as sugar beets are concerned the translocation or spreading of cytokinin will increase the leaf size, protein content, chlorophyll and leaf life. Hence, the photosynthetic power of the plant would be increased with cytokinin translocation which would result in increased carbohydrate synthesis and increase the stored carbohydrate content of the root.

Aqueous seaweed extracts have successfully been used as fertilizer additives on bananas, gladiolas, tomatoes, peppers, potatoes, corn and oranges with varying degrees of success. Of special interest was the increased uptake of manganese in banana plants. Also of interest was the improved storage of peaches.

The class of phytohormones referred to as auxins may be natural or synthetic such as indoleacetic acid or 2.4-dichlorophenoxy acetic acid (b 2.4D.). These hormones are transported within the root from its base to its apex. Natural occurring auxins are not as stable in ambient air as synthetic auxins. Auxins in general move more rapidly to the root tip when applied to cotyledon or leaves. The movement presumably is accompanied with the transport of carbohydrates via the phloem. Since auxins, as contrasted to cytokinins, move more rapidly through the plant they are adapted to the treatment of seeds prior to planting. The consistent application of phytohormones helps reduce the usage of N.P.K. fertilizers by as much as 25%. Optimally, cytokinins, auxins, and gibberellin(s) are applied at a rate of 0.001 to 4.0 grams per acre (or 0.0025 to 9.9 grams per hectare). Preferably these phytohormones are utilized as dilute solutions containing on the order of 10-200 wppm of active ingredient and, if used in an alkaline media, are stabilized by a preservative such as sodium benzoate.

The root of a plant contains portions of the best known phytohormones and serves as a center for synthesis. The xylem and phloem being the major circulatory portions of a plant also serve as hormone carriers for those hormones that can be translocated. It has been documented that there are manifold effects of root hormones, especially cytokinins, on shoot development. These include control of protein and $CO_2$ metabolism in leaves, enzyme formation in leaves, leaf aging and senescence, shoot elongation, stem elongation, lateral shoot development and release of floral bud dormancy, and fruit set.

Environmental influences which affect the root system such as water stress, flooding, excessive heat or cold act not only on water and ion uptake and transport of organic substrates but also on the hormonal flow from root to shoot and vice versa.

The amounts and relative ratios of the gibberellin, cytokinin and auxins employed in the compositions of the present invention may vary widely. Preferred compositional amounts for these active media are provided in Table 1. Where the composition includes a plurality of different gibberellins, cytokinins or auxins, the compositional ranges provided below are based on the total amount of the specified plant growth regulator, e.g., total amount of $GA_4$ and $GA_7$ collectively if both are used together in the formulation.

TABLE 1

Preferred Compositional Ranges for Plant Growth Regulators (wt. % based on total granule weight)

| Gibberellin | 0.001-10 | 0.03-3 | 0.1-1 |
| Cytokinin | 0.001-10 | 0.07-7 | 0.1-1.5 |
| Auxin | 0.001-10 | 0.04-4 | 0.1-1 |

In one embodiment, the ranges for the three components are preferably combined in more general to more narrow ranges. In a further embodiment, any of the preferred ranges may be combined with any of the more general ranges The specific combination of gibberellin, cytokinin, and auxin employed may vary, but preferred non-limiting combinations are provide in Table 2, below.

TABLE 2

Preferred Gibberellin, Cytokinin and Auxin Combinations

| Gibberellin | Cytokinin | Auxin |
|---|---|---|
| $GA_{4/7}$ | Kinetin | IBA |
| $GA_{4/7}$ | Kinetin | NAA |

TABLE 2-continued

Preferred Gibberellin, Cytokinin and Auxin Combinations

| Gibberellin | Cytokinin | Auxin |
|---|---|---|
| $GA_{4/7}$ | 6-BAP | IBA |
| $GA_{4/7}$ | 6-BAP | NAA |
| $GA_{4/7}$ | CPPU | IBA |
| $GA_{4/7}$ | CPPU | NAA |
| $GA_5$ | Kinetin | IBA |
| $GA_5$ | Kinetin | NAA |
| $GA_5$ | 6-BAP | IBA |
| $GA_5$ | 6-BAP | NAA |
| $GA_5$ | CPPU | IBA |
| $GA_5$ | CPPU | NAA |
| $GA_3$ | Kinetin | IBA |
| $GA_3$ | Kinetin | NAA |
| $GA_3$ | 6-BAP | IBA |
| $GA_3$ | 6-BAP | NAA |
| $GA_3$ | CPPU | IBA |
| $GA_3$ | CPPU | NAA |

In a more general preferred embodiment, any of the gibberellins which are described as preferred above (in the preceding paragraphs) may be combined with the any of the cytokinins described as preferred above, any of which combination may be combined with the any of the auxins described as preferred above.

Surfactant

In the formulation, a surfactant is preferably employed, and it may function as a wetting agent, as well as a dispersing and granulating aid. Suitable surfactants include non-ionic surfactants, anionic surfactants and amphoteric surfactants.

Non-ionic surfactants may include ethoxylated sorbitan esters such as EMSORB, TWEEN, and T-MAZE; sorbitan fatty acid esters such as SPAN and ALKAMUL; sucrose and glucose esters and derivatives thereof such as MAZON, RHEOZAN and GLUCOPON; ethoxylated alcohols such as TRYCOL, BRIJ, ARMIX and PLURAFAC; ethoxylated alkylphenols such as IGEPAL, MACOL and TERGITOL; ethoxylated fatty amines such as TRYMEEN and ETHOMEEN; ethoxylated fatty acids such as EMEREST, ALKAMUL and TRYDET; ethoxylated fatty esters and oils such as ALKAMUL and ATLAS G; fatty acids such as ATLAS G-1556; glycerol esters such as MAZOL GMO; glycol esters such as GLYCOL SEG; lanolin-based derivatives such as AMERCHOL CAB; methyl esters such as OLEOCAL ME; monoglycerides and derivatives such as ETHOSPERSE G-26; propoxylated and ethoxylated fatty acids such as ANTAROX AA-60; block copolymers of ethylene oxide (EO) and propylene oxide (PO) such as PLURONIC or SURFONIC; silicone-based surfactants such as SILWET, BREAKTHRU and mixtures of organosilicon surfactant with non-ionic or ionic surfactants; polysaccharides, copolymers of acrylamide and acrylic acid; and acetylenic diol derivatives such as SURFYNOL 104 or tristyrylphenols such as SOPROPHOR among others. Ethoxylated sorbitan esters may also be employed as surfactant. Non-ionic surfactants such as polyoxyethylene (20) monolaurate (TWEEN 20 or POLYSORBATE 20) may also be used.

Suitable anionic surfactants include phosphate esters such as EMPHOS and RHODAFAC; sulfates and sulfonates of oils and fatty acids such as POLYSTEP; sulfates and sulfonates of ethoxylated alkylphenols such as TRITON X-301; sulfates of dodecyl and tridecylbenzenes such as CALMULSE; sulfonates of condensed naphthalenes such as VULTAMOL; sulfonates of naphthalene and alkyl naphthalene such as MORWET and sulfosuccinates and derivatives such as MONAWET, among others.

Suitable amphoteric surfactants include lecithin and lecithin derivatives; and imidazolines and imidazoline derivatives such as MIRANOL, among others.

Preferred surfactants include non-ionic block copolymer surfactants and anionic sulfonates. More preferred surfactants include those selected from the group consisting of alkylarylsulphonates, like alkylnaphthalene sulphonates, and polyethoxylate-propoxylate block-copolymers such as oxoalcohol PO-EO adducts, and salts and mixtures thereof.

The trade names used above for binders and surfactants often are common to a class or series of binders or surfactants. Therefore, where a tradename is mentioned, any binder or surfactant in the family including that tradename will be suitable.

If incorporated in the formulation, the amount of surfactant employed may vary depending largely on the type of surfactant, carrier medium and specific active media employed. In preferred embodiments, the composition comprises the surfactant in an amount from 1 to 20 wt. %, e.g., from 1 to 10 wt. % or from 3 to 9 wt. %, based on the total weight of the composition.

Optional Carriers

As indicated above, the granulated formulations of the invention also include one or more carrier/fillers, preferably one or more inert carriers. Examples of carriers include inorganic minerals such as kaolin, mica, gypsum, fertilizer, carbonates such as magnesium carbonates, sulfates, or phosphates, sodium aluminosilicate, organic materials such as sugar, starches or cyclodextrins. Combinations of these various carriers may also be employed. Preferred carriers include sugars.

The granule compositions of the invention preferably comprise the carrier medium in an amount from 30 to 99 wt. %, e.g., from 70 to 99 wt. %, or from 85 to 95 wt. %, based on the total weight of the composition.

It should be noted that, in some embodiments, the carrier may be a fully dissolving carrier, while in other embodiments, the carrier may be dispersible but not soluble in water. Accordingly, when indicated herein that the plant growth regulating compositions are "water soluble," it is meant that the active ingredients are water soluble, and optionally the carrier is water soluble.

The carrier more preferably includes a saccharide, such as for example a disaccharide. Suitable saccharides include those described in U.S. Pat. No. 6,984,609, incorporated herein by reference in its entirety. The saccharide may be used as a diluent and as a granulating aid in the formulation. Suitable saccharides include sucrose, lactose and maltose, hydrolyzed starches such as maltodextrin and corn syrup solids, sugar alcohols such as sorbitol and mannitol and other sugars such as fructose and glucose among others. A presently preferred disaccharide is lactose monohydrate. A preferred carrier is lactose, for example lactose monohydrate, e.g., commercially available as LACTOPUR products.

Optional Binder

The formulation optionally includes one or more binders, which aid in binding, disintegration and solubilization of the formulation. The use of binders is preferred, in case the carrier material by itself is less effective in an extrusion process. Suitable binders include alkylated vinyl pyrrolidone copolymers such as AGRIMER AL-10 and AGRIMER AL-10LC; cross-linked polyvinylpyrrolidones such as AGRIMER AT and AGRIMER ATF; copolymers of vinyl acetate and vinylpyrrolidone such as AGRIMER VA-6 and AGRIMER VA-7; lignosulfonates and sodium or calcium salts thereof such as MARASPERSE, VANISPERSE, BORRESPERSE, NORLIG, POLYFON and KRAFTSPERSE; unsulfonated lignins such as INDULIN AT; clays such as HYDRITE RS, microcrystalline celluloses such as AVICEL PH and LATTICE NT; methyl cellulose ethers such as METHOCEL; ethyl cellulose polymers such as ETHOCEL; starch (natural or modified); gluten; silicates and sodium or calcium salts thereof; magnesium aluminum silicates such as VEEGUM F; natural or modified lecithins such as BEAKIN, CENTROMIX or YELKIN; sugar alcohols such as NEOSORB, SORBOGEM, MANOGEM and MALTISWEET and polyethylene glycols, among others. Polyvinylpyrrolidone such as AGRIMER 15, AGRIMER 30, AGRIMER 60, AGRIMER 90 and PLASDONE may also be used as binder. In case a binder is used, it is used in small quantities, such as for example 0.1 to 10 wt. %, e.g., from 0.5 to 8 wt. %, from 0.8-5 wt. %, or from 1-2 wt. %. Preferred binders are vinylpyrrolidones, cellulose ethers or polyethyleneglycols, as described above.

Optional Auxiliary Nutrients

The growth of a plant is regulated in an orderly way through photosynthesis and respiration. This is accomplished by sun, water, micronutrients such as molybdenum, manganese, zinc, iron and boron and enzymes and by growth hormones. In particular, metals and plant growth hormones are inseparably connected.

Dimethylallylaminopurine has been identified with the transfer of ribonucleic acid which combines with serine and tyrosine before these amino acids are incorporated into protein. This explains the cytokinin effect on ribonucleic acid, protein and chlorophyll levels, and indirectly plant growth. Zinc, manganese and iron are all involved in the process of plant growth. Magnesium is essential to chlorophyll formation.

Manganese activates the enzyme indoleacetic acid oxidase which controls the distribution of the growth regulators produced from auxins. This enzyme limits the amount of auxin in any area and prevents excessive amounts. It also deactivates auxin in nongrowing areas.

Zinc builds up the auxin hormone just as manganese regulates and controls the supply.

Iron activates an enzyme transport system that controls directions and movement of plant regulators.

Other minerals such as copper, boron, molybdenum, and magnesium also have important functions in plants.

In view of the importance of metals in plant growth, the plant growth regulating compositions of the invention optionally further comprise one or more metal-containing auxiliary nutrients, e.g., micronutrients. The chemical characteristics of the auxiliary nutrients are dictated by several factors. The purity of the selected carrier greatly influences the rate of absorption and distribution of nitrogen, phosphate and potassium nutrients by plant tissues.

In preferred embodiments, the composition comprises one or more micronutrients, preferably one or more chelating agents, optionally to provide a metal concentration from 1 to 15 wt. %, e.g., from 2 to 12 wt. % or from 4 to 10 wt. %, based on the total weight of the composition (i.e., the granules). Preferred chelating agents include any metal EDTA or citrate salt of a transition metal, preferably of zinc, copper, manganese, magnesium, iron, copper, boron, or molybdenum.

In another aspect, the composition comprises one or more nitrogen sources, such as urea, ammonium nitrate, ammonium sulfate, or a urea clathrate. Such nitrogen sources may be provided in an amount effective to provide a nitrogen content from 1 to 30 wt. %, e.g., from 2 to 20 wt. % or from 4 to 15 wt. %, based on the total weight of the composition (i.e., the granules). In one embodiment, a blend of a polyoxyethylene alcohol and a urea clathrate may be employed, such as ATPLUS UCL1007, optionally in an amount from 1 to 20 wt. %, e.g., from 1 to 10 wt. % or from 10 to 20 wt. % based on the total weight of the composition.

Based on the aforementioned criteria, the auxiliary nutrients selected for use in association with the growth enhancing compositions of the present invention may comprise ammonium thio-sulfate, ammonium polysulfate, 75-85% technical grade phosphoric acid and 45% potassium hydroxide solution; and dry solubles comprising tri-potassium polyphosphate, potassium phosphates, technical grade diammonium phosphate-ammonium phosphate containing no more than 3% by weight of the impurity tri-calcium phosphate, and feed grade urea of low biuret manufacture.

In some embodiments, the plant growth regulating composition of the invention further comprises one or more amino acids, optionally an amino acid selected from the group consisting of Arginine, Histidine, Lysine, Aspartic Acid, Glutamic Acid, Serine, Threonine, Asparagine, Glutamine, Cysteine, Selenocysteine, Glycine, Proline, Alanine, Valine, Isoleucine, Leucine, Methionine, Phenylalanine, Tyrosine, and Tryptophan, with a preference for Alanine and Tryptophan. Preferred amino acids include forms or derivatives of Proline, for example L-Proline, and forms or derivatives of Glycine, for example Glycine Betaine, and combinations thereof. The amino acid can be present at a range of levels within the plant growth regulating composition, for example from 1-40 wt. %, e.g., from 2-30 wt. %, from 5-25 wt. %, or from 10-20 wt. %.

Optional Supplemental Active Ingredients

It is also contemplated that the materials of this invention may be used in combination with other essential biologicals or beneficial microorganisms or active ingredients, such as herbicides, anti-microbials, fungicides, insecticides, nematicides, biological pesticides such as microbial pesticides, biochemical pesticides (semiochemicals, hormones or natural plant regulators), plant produced pesticides (botanicals) or plant nutrients.

Optional Adjuvants

Other components of the formulation may include additional surface active agents, stickers, spreader stickers, preservatives, humectants, dyes, U.V. (ultra-violet) protectants, buffers, acidifiers, compatibility agents, flow agents, antifoams, antioxidants, petroleum-based oils, vegetable based oils, or other components that facilitate product handling and application. A preferred antifoam is polydimethylsiloxane. The optional adjuvants may be applied, for example, at a rate ranging from 0.125 to 0.5% v/v.

Acidifiers, such as citric acid, phosphoric acid and derivatives thereof, e.g., phosphate ester surfactants, optionally in an amount from 0.01 to 1 wt. %, may be used to reduce pH resulting in the facilitation of carboxylic acid dissociation allowing some active media, for example, gibberellins, to be more easily taken up into the plant. Preferably, when dissolved in water, the granules of the invention provide a pH ranging from 4 to 8, e.g., from 5 to 7.

Method of Making Granules

The granules of the invention may be formed by a variety of processes, such as agglomeration granulation, pan granulation, or spray drying. In a preferred embodiment, the water soluble plant growth regulating compositions of the invention are formed by a milling and extrusion process. For example, the of the present invention may be formed through milling and extrusion process. The gibberellin, cytokinin and auxin may be separately passed through a mill, e.g., jet or hammer mill, to reduce their particle size to on the order of from 1 to 5 μm. The resulting powder is preferably dry mixed, optionally with a dry surfactant powder, to form a powder mixture. The resulting powder mixture may then be further milled, preferably air milled, to further reduce particle size.

After further milling, the powder mixture may be combined with carrier medium and blended, e.g., in a powder blender, to form a blended mixture. Water is preferably added to the blended mixture in an amount sufficient to form an extrudable paste or dough, while preferably mixing continuously. Water is typically added in an amount from 12-14 wt. %, although the amount may vary depending on scale and equipment.

The resulting paste is then extruded, preferably through a screen, to form granules of the desired diameter, which may be recycled to make more granules. The screen preferably comprises a 0.5 to 2.0 mm mesh size, e.g., 0.5 to 1.0 mm mesh size or about 0.8 mm mesh size. The resulting extrudate is then dried, preferably in a fluid bed drier, to a moisture content of less than 10 wt. %, e.g., less than 5 wt. % or less than 3 wt. %. Fine particles may be removed, e.g., through a cyclonic or screen separation process, during or after the drying step.

Application

Once formed, the precise amount of plant growth regulating composition employed in treating plants or seeds will depend largely upon the type of response desired, the formulation used and the type of plant species or seed treated. For example, when applied in seed treatment, the composition may be applied in an amount sufficient to provide a cytokinin concentration from 0.265 to 0.106 grams per 100 pounds seed, an auxin concentration from 0.0133 to 0.0532 grams per 100 pounds seed, and a gibberellin concentration from 0.0089 to 0.0356 grams per 100 pounds. When applied in furrow (foliar application), the composition may be applied in an amount sufficient to provide a cytokinin concentration from 0.0795 to 0.159 grams per acre, an auxin concentration from 0.0399 to 0.0798 grams per acre, and a gibberellin concentration from 0.0267 to 0.0534 grams per acre. For in furrow application, water may be added to the granules in an amount to provide a cytokinin concentration from 0.84 to 14.05 wppm, an auxin concentration from 0.42 to 7.02 wppm and a gibberellin concentration from 0.28 to 4.70 wppm. For in-furrow/foliar applications, typical spray volumes may range from 2 to 35 gallons per acre. This provides active ingredient concentrations as follows: (1) gibberellin: from 0.2 to 7.0 wppm (0.0267 g/35 gal to 0.0534 g/2 gal); (2) cytokinin: from 0.6 to 20.9 wppm (0.0795 g/35 gal to 0.159 g/2 gal); (3) auxin: from 0.3 to 10.5 wppm (0.0399 g/35 gal to 0.0798 g/2 gal). In a further embodiment, the ranges described in this paragraph are preferred ranges, of which the skilled person will understand, can be combined with other specifically mentioned and/or preferred constituents of the composition.

The following examples are illustrative of the wide range of plant growth responses that can be realized by application of a preferred composition of the present invention to various plant species. Nevertheless, there is no intention that the invention be limited to these optimum ratios of active components since workers in the art will find the compositions of the invention set forth hereinabove to be effective growth enhancers. Also, it should readily occur to one skilled in the art that the recognition of improved results using the compositions according to the present invention in connection with other plants, seeds, fruits and vegetables not specifically illustrated herein is readily within the capabilities of one skilled in the art.

EXAMPLES

Preparation of Examples A-D

A water soluble plant growth regulating composition in granule form was produced in Examples A-D by a milling and extrusion process. The dry powder ingredients were bag mixed thoroughly. The resulting powder mixture was hammer milled through a 0.8 mm screen. Water was added gradually to the powder while mixing in a Kenwood food processor until a doughy material suitable for extrusion was formed. The doughy material was extruded through a 0.8 mm screen using a Kuji benchtop KAR75 extruder. The resulting granules were tray dried in an oven at 55° C. for approximately 4 hours. The dried granules were sieved through 2 mm & 0.25 mm screens to remove oversized particles and fines.

The gibberellin employed was $GA_4$ (92% pure), the cytokinin employed was kinetin (98.5% pure), and the auxin employed was indole-3-butyric acid (98% pure). The surfactants employed in Examples A and D included a sodium salt of naphthalene sulfonate condensate (NSC) powder (MORWET D-425, Akzo-Nobel) and sodium isopropyl naphthalene sulfonate (SINS) powder (MORWET IP, Akzo Nobel). Example B did not include a surfactant. Example C included a $C_{12}/C_{15}$-Oxo-alcohol PO-EO adduct surfactant (GENAPOL EP 2552, AAKO). The carrier medium employed was lactose monohydrate (LACTOPUR 216). Granules having an average particle size of 1 mm were formed having the following compositions.

TABLE 3

Example Granule Composition (% w/w)

| Example | A | B | C | D |
|---|---|---|---|---|
| Gibberellin $GA_4$ tech (92%) | 0.27 | 0.27 | 0.27 | 0.27 |
| Indole-3-butyric acid tech (98%) | 0.38 | 0.38 | 0.38 | 0.38 |
| Kinetin tech (98.5%) | 0.77 | 0.77 | 0.77 | 0.77 |
| NSC Powder | 3.75 | — | — | 3.75 |
| SINS Powder | 1.88 | — | — | 1.88 |
| $C_{12}/C_{15}$-Oxo-alcohol PO-EO adduct | — | — | 2.50 | — |
| Lactose monohydrate carrier | 92.95 | 98.58 | 96.08 | 92.95 |
| Water, as wt. % of dry powder | 10 | 11 | 8.2 | 8.6 |
| Batch Size, g | 500 | 500 | 720 | 500 |

Evaluation of Examples A-D

The inventive granules surprisingly and unexpectedly exhibited good physical and chemical stability for all three plant growth regulators. The granules were tested before and after storage for 2 weeks at 54° C. in a controlled temperature storage cabinet. The following assessments were made (active content method is reverse phase HPLC).

TABLE 4

Granule Testing Parameters

| Test | Method | Detail |
|---|---|---|
| Appearance | Visual | State, color, granule integrity |
| pH | CIPAC MT75.3 | 1% dilution in deionized water |
| Wettability | CIPAC MT53.3 | CIPAC D |
| Wet sieve retention | CIPAC MT167 | 150 & 45 µm sieves |
| Persistent foam | CIPAC MT47.2 | 1% in CIPAC D |
| Suspensibility | CIPAC MT184 | 1% in CIPAC D water @ 30° C. |
| Dilution stability | CIPAC MT179 | 5 g in CIPAC D |
| Density | CIPAC MT169 | Bulk & Tap |
| Active content | Intertek 1324707 | |

Concentrations of the plant growth regulators may be increased significantly, along with the optional inclusion of micronutrients, and adjuvants, as described above.

Appearance

The inventive granules appeared as cylindrical light brown granules, 3-9 mm in length. The granules visibly retained their integrity on storage. Example A granules were larger than the others due to slightly higher moisture content on extrusion. Example B granules were the smallest due to low moisture content on extrusion. Example C granules exhibited a "speckled" appearance likely due to a very small quantity of product adhering to the glass bottle.

Moisture Content after Drying

All samples had a moisture content after drying in the range 4.6-4.9% w/w.

pH

For all samples, 1% dilutions gave pH values in the range 4.2-4.8, with no significant changes on storage.

Wettability

All granules had good wettability of less than 5 seconds.

Wet Sieve Residue

All samples were well within normally acceptable limits (less than 2% on a 75 µm sieve). Example C gave the highest value and Example A gave the lowest value.

Persistent Foam

All granules gave little foam on dilution, i.e., a maximum of 2 ml foam after 1 minute.

Suspensibility

The mass of residue was similar for all samples, in the range 0.26-0.29 g.

Dilution Stability

Example C gave the greatest residue, but all samples were well within normally acceptable limits.

Densities

Densities were generally similar for all samples. Bulk densities were in the range 0.415-0.484 g/ml. Tap densities were in the range 0.466-0.540 g/ml.

Active Content

The three active components in the examples exhibited the desired stability after storage for 2 weeks at 54° C. and met or exceeded Food & Agriculture Organization of the United Nations (FAO) specifications for active ingredient concentration.

Preparation of Examples E-P

To produce water soluble plant growth regulating compositions in granule form for Examples E-P, the following materials were pre-milled prior to blending with other ingredients: Indole-3-butyric acid, Kinetin tech, and Gibberellins $GA_{4/7}$ (if required by the formulation) were all milled through a Retzsch Rotor Beater mill with 0.5 and 1.0 mm screens. For formulations containing magnesium sulfate, magnesium sulfate was milled through a Retzsch Rotor Beater mill with a 1.0 mm screen. Additionally BAP, Gibberellin $GA_3$, and sodium NAA, where applicable, were passed through a bench top hammer mill with no screen fitted. After the pre-milling, all the dry powder ingredients were mixed thoroughly. The resulting powder base was passed through a hammer mill. Water was added gradually to the powder base to make a wetted mass suitable for extrusion. The wetted mass was then extruded through a 0.8 mm screen. The resulting granules were tray dried in an oven at 50° C. for approximately 1 hour either tray dry or fluid bed dry using MP1. The dried granules were sieved through 2 mm & 0.25 mm screens to remove oversized particles and fines.

Evaluation of Examples E-L

For Examples E-L, granules were prepared having the following compositions.

TABLE 5

Example Granule Composition (% w/w)

| | Example | | | | | | | |
|---|---|---|---|---|---|---|---|---|
| | E | F | G | H | I | J | K | L |
| Gibberellin $GA_{4/7}$ | | 0.25 | 0.25 | 2.5 | 12.5 | 0.25 | 0.032 | 0.25 |
| Gibberellin $GA_3$ | 0.25 | | | | | | | |
| Indole-3-butyric acid | 0.37 | | 0.37 | 3.7 | 18.5 | 0.37 | 0.046 | 0.37 |
| Sodium NAA | | 0.41 | | | | | | |
| Kinetin | 0.76 | 0.76 | | 7.6 | 38.0 | 0.76 | 0.092 | 0.76 |
| BAP | | | 0.76 | | | | | |
| (NSC) powder | 3.75 | 3.75 | 3.75 | 3.75 | 3.75 | 3.75 | 3.75 | |
| SINS Powder | 1.88 | 1.88 | 1.88 | 1.88 | 1.88 | 1.88 | 1.88 | |
| Atplus UCL 1007 | | | | | | | | 10.0 |
| Zinc EDTA (tetrahydrate) | | | | | | | 9.02 | |
| Manganese EDTA (assumed anhydrous) | | | | | | | 6.44 | |
| Copper EDTA (anhydrous) | | | | | | | 1.27 | |
| Lactose monohydrate carrier | 92.9 | 92.9 | 92.9 | 80.6 | 23.1 | | 77.5 | 88.6 |
| Magnesium sulfate | | | | | | 92.9 | | |
| Water, as wt. % of dry powder | 7.8 | 7.2 | 7.9 | 8.1 | 9.2 | 4.3 | 8.2 | 7.2 |
| Batch Size, kg | 1.0 | 1.0 | 1.0 | 0.9 | 0.9 | 0.9 | 0.9 | 0.9 |

All batches processed satisfactorily except for those containing an alternative water soluble filler. Batches with magnesium sulfate as a water soluble filler could be extruded, but gave a low yield of dusty granules. Using ammonium sulfate or sodium sulfate as a water soluble filler gave materials that were unextrudable. It is expected that such filler materials can suitably be used if combined with a minor amount of binder to aid extrusion.

The inventive granules surprisingly and unexpectedly exhibited good stability for all three plant growth regulators. The appearance of the granules was observed before and after storage for 2 weeks at 54° C.; 4 weeks at 50° C., 25° C., and 0° C. in a controlled temperature storage cabinet. The only change in appearance observed was a change in color for Examples J and K after 4 weeks of storage.

Evaluation of Examples M-P

Examples M-P were prepared according to the same procedure as Examples E-L above. Granules were formed having the following compositions.

TABLE 6

Example Granule Composition (% w/w)

| Example | M | N | O | P |
|---|---|---|---|---|
| Gibberellin $GA_{4/7}$ | 0.25 | 0.0047 | | 0.0047 |
| Gibberellin $GA_3$ | | | 0.032 | |
| Indole-3-butyric acid | 0.37 | 0.007 | 0.046 | 0.007 |
| Kinetin | 0.76 | 0.0141 | 0.092 | 0.0141 |
| (NSC) powder | 3.75 | 3.75 | 3.75 | 3.75 |
| SINS Powder | 1.88 | 1.88 | 1.88 | 1.88 |
| Zinc (EDTA) (tetrahydrate) | | 70.19 | | 70.19 |
| Zinc citrate (dehydrate) | 38.9 | | 3.89 | |
| Manganese citrate (anhydrous) | 30.0 | | 3.0 | |
| Copper citrate (pentahydrate) | 7.0 | | 0.7 | |
| L-Proline | | | | 1.58 |
| Lactose monohydrate carrier | 17.0 | 24.2 | 86.6 | 22.6 |

TABLE 6-continued

Example Granule Composition (% w/w)

| Example | M | N | O | P |
|---|---|---|---|---|
| Water, as wt. % of dry powder | 12.0 | 6.5 | 7.0 | 7.0 |
| Batch Size, kg | 0.9 | 0.9 | 0.9 | 0.9 |

All batches processed satisfactorily. Example N produced a quantity of fines, which required the preparation of a second batch to have sufficient material for field trials.

The inventive granules surprisingly and unexpectedly exhibited good physical and chemical stability for all three plant growth regulators. The granules were evaluated before and after storage for 2 weeks at 54° C.; 4 weeks at 50° C., 25° C., and 0° C.; and 8 weeks at 40° C. in a controlled temperature storage cabinet. The following assessments were made.

Active Content

The active ingredient concentration of Example M was determined initially and after 2 weeks at 54° C. using reverse phase HPLC.

TABLE 7

Active Ingredient Content for Example M

| Active Ingredient | GA4/7 | Kinetin | IBA |
|---|---|---|---|
| Initial amount (% w/w) | 0.288 | 0.693 | 0.393 |
| After 2 weeks at 54° C. (% w/w) | 0.283 | 0.692 | 0.387 |
| % of Initial Amount after 2 weeks | 98.3 | 99.9 | 98.5 |

All three active ingredients had good chemical stability after 2 weeks at 54° C.

Appearance

The only change in appearance for Examples M-P observed over the 8 week evaluation was a change in color for Example P when stored at 50° C. and 54° C.

pH pH for Examples M-P was measured using the method CIPAC MT75.3 with a 1% dilution in deionized water. The results are shown below.

TABLE 8 pH for Examples M-P

| Example | M | N | O | P |
|---|---|---|---|---|
| Initial pH | 4.5 | 8.5 | 4.8 | 7.1 |
| 2 weeks at 54° C. | 4.5 | 6.2 | 4.8 | 5.3 |
| 4 weeks at 50° C. | 4.4 | 6.7 | 4.8 | 5.6 |
| 4 weeks at 25° C. | 4.4 | 7.0 | 4.8 | 7.4 |
| 4 weeks at 0° C. | 4.4 | 7.6 | 4.8 | 7.4 |
| 8 weeks at 40° C. | 4.4 | 8.7 | 4.8 | 6.5 |

There was no significant change in pH for Examples M and O. Example P showed a decrease at 54° C., 50° C., and 40° C. Example N showed variability.

Wettability

Wettability was measured using method CIPAC MT53.3, Water CIPAC D. All four samples showed excellent and almost instantaneous wettability. There was no change in wettability after storage up to 8 weeks at 40° C.

Wet Sieve Retention

Wet sieve retention was measured using method CIPAC MT 167.

TABLE 9

Wet Sieve Retention for Examples M-P (% retained)

| | Example | | | | | | | |
|---|---|---|---|---|---|---|---|---|
| | M | | N | | O | | P | |
| | 150 μm | 45 μm | 150 μm | 45 μm | 150 μm | 45 μm | 150 μm | 45 μm |
| Initial | 3.2 | 13.8 | 0.02 | 0.03 | 0.5 | 6.4 | 0.03 | 0.04 |
| 2 weeks at 54° C. | 2.7 | 8.1 | 0.02 | 0.09 | 0.5 | 1.4 | 0.04 | 0.11 |
| 4 weeks at 50° C. | 2.4 | 7.0 | 0.05 | 0.30 | 1.2 | 2.4 | 0.03 | 0.06 |
| 4 weeks at 25° C. | 3.8 | 7.9 | 0.11 | 0.67 | 0.8 | 1.6 | 0.06 | 0.20 |
| 4 weeks at 0° C. | 3.5 | 5.3 | 0.05 | 0.09 | 0.6 | 1.0 | 0.02 | 0.10 |
| 8 weeks at 40° C. | 2.6 | 8.0 | 0.01 | 0.03 | 0.4 | 1.04 | 0.03 | 0.07 |

High initial sieve retentions were found for Examples M and O (which both contained metal citrates). Acceptable sieve retentions were found for Examples N and P initially and after 8 weeks.

Dilution Stability

Dilution stability for Examples M through P was measured using method CIPAC MT179 at 1.2% w/w in CIPAC D. No significant increase in wet sieve retention of the samples was observed after 18 hours for any of the samples initially or after storage.

Moisture Content

The moisture contents for Examples M through P were essentially unchanged from an initial measurement to measurements taken after 8 weeks of storage.

Therefore, it was observed from Examples E through P that it was possible to formulate the Examples, with some difficulty in granulating compositions that contained alternative water soluble fillers like magnesium sulfate. The only change in product characteristics after storage observed was a change in the color of samples J, K, and P. In addition, it was observed that the samples prepared containing metal citrates had a high sieve retention.

While the invention has been described in detail, modifications within the spirit and scope of the invention will be readily apparent to those of skill in the art. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by one of ordinary skill in the art. Furthermore, those of ordinary skill in the art will appreciate that the foregoing description is by way of example only, and is not intended to limit the invention.

We claim:

1. A water-soluble plant growth regulating composition in granule form, comprising an active medium, and a carrier medium in an amount from 70 to 99 wt. % based on the total weight of the composition, wherein the active medium comprises:
   (a) a gibberellin in an amount from 0.001 to 10 wt. % based on the total weight of the composition;
   (b) a cytokinin in an amount from 0.001 to 10 wt. %; and
   (c) an auxin 0.001 to 10 wt. %, based on the total weight of the granules.

2. The composition of claim 1, having a solubility greater than 1 g/100 g water at 25° C.

3. The composition of claim 1, further comprising a surfactant.

4. The composition of claim 3, wherein the surfactant is selected from the group consisting of: alkylnaphthalene sulphonates, oxoalcohol PO-EO adducts, and salts and mixtures thereof.

5. The composition of claim 3, wherein the surfactant is present in an amount from 1 to 20 weight percent.

6. The composition of claim 1, further comprising one or more micronutrients.

7. The composition of claim 6, wherein the one or more micronutrients comprise one or more chelating agents.

8. The composition of claim 7, wherein the chelating agents are selected from the group consisting of EDTA and citrate salts.

9. The composition of claim 6, wherein the one or more micronutrients comprise one or more nitrogen sources.

10. The composition of claim 1, further comprising one or more amino acids.

11. The composition of claim 1, wherein the gibberellin is selected from the group consisting of $GA_3$, $GA_4$, $GA_5$, $GA_7$ and combinations thereof.

12. The composition of claim 1, wherein the cytokinin is selected from the group consisting of kinetin, 6-benzylaminopurine (6-BAP), 1-(2-chloropyridin-4-yl)-3-phenylurea (CPPD), and thidizuron (TDZ).

13. The composition of claim 1, wherein the auxin is selected from the group consisting of 3-indolebutyric acid, 3-indoleacetic acid, 1-naphthylacetic acid, 3-indolebutyric acid, and salts and esters thereof.

14. The composition of claim 1, wherein the gibberellin comprises gibberellin GA4, the cytokinin comprises kinetin, and the auxin comprises indole-3-butyric acid.

15. The composition of claim 1, wherein the gibberellin comprises a mixture of gibberellin $GA_4$ and gibberellin $GA_7$.

16. The composition of claim 1, wherein the active medium has an average particle size from 1 to 5 μm as determined by laser diffraction particle size analysis.

17. The composition of claim 1, wherein the carrier medium comprises lactose monohydrate.

18. The composition of claim 1, wherein the carrier medium is water soluble.

19. A process for preparing a liquid plant growth regulating composition, comprising dissolving the composition of claim 1 in water to form the liquid plant growth regulating composition.

20. The process of claim 19, wherein water is provided in an amount sufficient to provide an auxin concentration from 0.3 to 10.5 wppm, a cytokinin concentration from 0.6 to 20.9 wppm and a gibberellin concentration from 0.2 to 7.0 wppm.

21. A process for regulating plant growth comprising:
   (a) dissolving the composition of claim 1 in water to form a liquid plant growth regulating composition; and
   (b) applying the liquid plant growth regulating composition to a plant or seed.

22. The process of claim 21, wherein step (b) comprises applying the liquid plant growth regulating composition to a seed, the process further comprising planting the seed.

23. The process of claim 21, wherein step (b) comprises applying the liquid plant growth regulating composition to a seed furrow during a planting operation.

24. The process of claim 21, wherein step (b) comprises applying the liquid plant growth regulating composition to a plant.

* * * * *